United States Patent
Clark

(12) 
(10) Patent No.: US 6,551,828 B1
(45) Date of Patent: Apr. 22, 2003

(54) COMPOSITIONS AND METHODS FOR GENERATING EXPRESSION VECTORS THROUGH SITE-SPECIFIC RECOMBINATION

(75) Inventor: Robin Clark, Benicia, CA (US)

(73) Assignee: Protemation, Inc., Bainbridge Island, WA (US)

( * ) Notice: Subject to any disclaimer, the term of this patent is extended or adjusted under 35 U.S.C. 154(b) by 96 days.

(21) Appl. No.: 09/606,323

(22) Filed: Jun. 28, 2000

(51) Int. Cl.[7] .................. C12N 15/87; C12N 15/63; C12N 15/85; G01N 33/567
(52) U.S. Cl. .................. 435/462; 935/28; 435/455; 435/471; 435/7.31; 435/7.32; 435/7.21
(58) Field of Search .................. 435/5, 7.31, 7.21, 435/7.32, 471, 455, 462; 935/28

(56) References Cited

U.S. PATENT DOCUMENTS 5,861,279 A * 1/1999 Zhnag et al. .............. 435/69.1

FOREIGN PATENT DOCUMENTS

| WO | WO 96/40724 | 12/1996 |
|----|-------------|---------|
| WO | WO 97/47758 | 12/1997 |
| WO | WO 99/21977 | 5/1999 |
| WO | WO 00/12687 | * 3/2000 |
| WO | WO 00/29000 | 5/2000 |
| WO | WO 00/52027 | 9/2000 |
| WO | WO 00/63410 | 10/2000 |
| WO | WO 01/05961 | 1/2001 |
| WO | WO 01/31039 | 5/2001 |

* cited by examiner

*Primary Examiner*—Andrew Wang
*Assistant Examiner*—Tomas Friend
(74) *Attorney, Agent, or Firm*—Shirley Chen; Wilson Sonsini Goodrich & Rosati

(57) ABSTRACT

Compositions, kits, and methods are provided for use in a recombinational cloning or subcloning methods for constructing expression vectors which comprise: ligating a library of double-stranded linear donor DNAs, where each member of the library includes a donor DNA sequence, with a double-stranded linear driver DNA which includes a promoter sequence and a donor recombination site to form a single circular donor DNA, the single circular donor DNA not including an origin of replication, where the donor DNA sequence is under the transcriptional control of the promoter; and contacting the circular donor DNA and a circular acceptor acceptor vector in the presence of a recombinase to form a single fused circular vector, the circular acceptor vector comprising an origin of replication and an acceptor recombination site capable of recombining with the circular donor DNA.

28 Claims, 2 Drawing Sheets

SEQUENCE LISTING

<160> NUMBER OF SEQ ID NOS: 7

<210> SEQ ID NO 1
<211> LENGTH: 34
<212> TYPE: DNA
<213> ORGANISM: Artificial Sequence
<220> FEATURE:
<223> OTHER INFORMATION: loxP

<400> SEQUENCE: 1
ataacttcgt ataatgtatg ctatacgaag ttat                                 34

<210> SEQ ID NO 2
<211> LENGTH: 34
<212> TYPE: DNA
<213> ORGANISM: Artificial Sequence
<220> FEATURE:
<223> OTHER INFORMATION: loxP511

<400> SEQUENCE: 2
ataacttcgt atagtataca ttatacgaag ttat                                 34

<210> SEQ ID NO 3
<211> LENGTH: 34
<212> TYPE: DNA
<213> ORGANISM: Artificial Sequence
<220> FEATURE:
<223> OTHER INFORMATION: loxC2

<400> SEQUENCE: 3
acaacttcgt ataatgtatg ctatacgaag ttat                                 34

<210> SEQ ID NO 4
<211> LENGTH: 34
<212> TYPE: DNA
<213> ORGANISM: Artificial Sequence
<220> FEATURE:
<223> OTHER INFORMATION: FLP

<400> SEQUENCE: 4
gaagttccta ttctctagaa agtataggaa cttc                                 34

-continued

```
<210> SEQ ID NO 5
<211> LENGTH: 10
<212> TYPE: PRT
<213> ORGANISM: Artificial Sequence
<220> FEATURE:
<223> OTHER INFORMATION: EE-tag

<400> SEQUENCE: 5

Met Glu Glu Glu Glu Tyr Met Pro Met Glu
1               5                   10

<210> SEQ ID NO 6
<211> LENGTH: 13
<212> TYPE: DNA
<213> ORGANISM: Artificial Sequence
<220> FEATURE:
<223> OTHER INFORMATION: SfiI restriction site
<221> NAME/KEY: misc_feature
<222> LOCATION: (5)..(9)
<223> OTHER INFORMATION: Residue "n" represents adenosine, guanosine,
      cytidine or thymidine

<400> SEQUENCE: 6
ggccnnnnng gcc                                                          13

<210> SEQ ID NO 7
<211> LENGTH: 8
<212> TYPE: DNA
<213> ORGANISM: Artificial Sequence
<220> FEATURE:
<223> OTHER INFORMATION: NotI restriction site

<400> SEQUENCE: 7 gcggccgc                                                                 8
```

COMPOSITIONS AND METHODS FOR GENERATING EXPRESSION VECTORS THROUGH SITE-SPECIFIC RECOMBINATION

FIELD OF THE INVENTION

This invention relates to recombinant DNA technology, nucleic acids, vectors and methods for use in a recombinational cloning or subcloning, and more specifically for constructing expression vectors by using recombination proteins in vitro or in vivo through site-specific recombination.

DESCRIPTION OF RELATED ART

Recombinant DNA technology, also called gene cloning or molecular cloning, is widely used to transfer genetic information, i.e. DNA, from one organism to another. A typical recombinant DNA experiment often follows the following procedure. First, the DNA (e.g., the cloned DNA, insert DNA, target DNA, or foreign DNA) from a donor organism is extracted, enzymatically cleaved (or cut/digested), and joined (ligated) to another DNA entity (e.g. a cloning vector) to form a new, recombinant DNA molecule (or cloning vector-insert DNA construct). Second, this cloning vector-insert DNA construct is transferred into and maintained within a host cell, such as transformation of a bacterial host cell by the construct. Third, those host cells that take up the DNA construct (transformed cells) are identified and selected from those that do not. In addition, if required, a DNA construct can be prepared to ensure that the protein product that is encoded by the cloned DNA sequence is produced by the host cell.

Accordingly, this traditional cloning methods using restriction enzymes and ligase can be time consuming, especially when a specific expression vector is required for transferring the target gene into a heterologous host cell, such as a mammalian cell. The specific expression vector may not contain matching restriction sites for the donor DNA. Extensive reengineering of the expression vector may be required to introduce the matching restriction sites into the vector so that the vector and the insert DNA can be ligated to produce the final construct. Alternatively, multiple restriction enzymes may have to be employed to generate an insert DNA having suitable restriction sites for ligation with the vector. In this case, reaction conditions for each restriction enzyme may differ such that it is often necessary to perform a few separate restriction digestion reactions to obtain the desired insert. Further, the efficiency of direct ligation between the vector and insert may be very low, especially between large fragments. As a result, the whole procedure is tedious, and the final yield of the correctly ligated construct can be low.

Site-specific recombination represents another useful method of recombinant DNA technology. This method employs a site-specific recombinase, an enzyme which catalyzes the exchange of DNA segments at specific recombination sites. Site-specific recombinases present in some viruses and bacteria, and have been characterized to have both endonuclease and ligase properties. These recombinases, along with associated proteins in some cases, recognize specific sequences of bases in DNA and exchange the DNA segments flanking those segments. Landy, A. (1993) Current Opinion in Biotechnology 3:699–707.

A typical site-specific recombinase is Cre recombinase. Cre is a 38-kDa product of the cre (cyclization recombination) gene of bacteriophage P1 and is a site-specific DNA recombinase of the Int family. Sternberg, N. et al. (1986) J. Mol. Biol. 187: 197–212. Cre recognizes a 34-bp site on the P1 genome called loxP (locus of X-over of P1) and efficiently catalyzes reciprocal conservative DNA recombination between pairs of loxP sites. The loxP site consists of two 13-bp inverted repeats flanking an 8-bp nonpalindromic core region. Cre-mediated recombination between two directly repeated loxP sites results in excision of DNA between them as a covalently closed circle. Cre-mediated recombination between pairs of loxP sites in inverted orientation will result in inversion of the intervening DNA rather than excision. Breaking and joining of DNA is confined to discrete positions within the core region and proceeds on strand at a time by way of transient phophotyrosine DNA-protein linkage with the enzyme. Other examples of site-specific recombination systems include the integrase/att system form bacteriophage λ and the FLP/FRT system from the *Saccharomyces cerevisiae* 2pi circle plasmid.

These site-specific recombination systems have been used in vivo to facilitate recombination between different vectors. Waterhouse et al. used an in vivo method to join light and heavy chains of an antibody. The light and heavy chains were cloned in different phage vectors between loxP and loxP 511 sites that were used to transform new *E. coli* cells. Waterhouse, P. et al. (1993) Nucleic Acid Res. 21:2265–2266. Cre acted on two parental molecules, one plasmid and another phage, in the host cells to produce four products in equilibrium: two different cointegrates (produced by recombination at either loxP or loxP511 sites), and two daughter molecules, one of which was the desired product. Schlake and Bode used an in vivo method to exchange expression cassettes at defined chromosomal locations, each flanked by a wild type and spacer-mutated FRT recombination site. Schlake and Bode (1994) Biochemistry 33:12746–12751. A double-reciprocal crossover was mediated in cultured mammalian cells by using the FLP/FRT system for site-specific recombination. Aoki et al. used a shuttle plasmid (pAdMCS) that carried a gene of interest, a loxP site, the adenoviral 5-LTR and packaging signal 0 to 1 mu, and a multiple cloning site. Aoki et al. (1999) Mol. Med. 5:224–231. The shuttle plasmid was linearized by a restriction enzyme NheI and recombined with ClaI-digested adenoviral cosmid in vitro. Cre recombinase produced the full-length recombinant adenoviral vector in vitro by an exchange of region distal to the loxP site linearized in these two molecules.

SUMMARY OF THE INVENTION

The present invention relates to compositions, kits, and methods for use in a recombinational cloning or subcloning. In particular, the present invention provides novel methods for constructing expression vectors by using site-specific recombinases in vitro. These method may be used for high throughput screening of genes, functional genomics and other human genome projects.

In one aspect, the present invention provides a double-stranded circular donor DNA for transferring a donor DNA sequence into expression vectors. The circular donor DNA comprises: a donor DNA sequence; a donor recombination site; at least one selectable marker, the circular donor DNA not including an origin of replication.

The donor DNA sequence may be any gene of interest or any synthetic DNA sequence which is needed to be transferred into an expression vector. For example the donor DNA segment may be a sequence derived from cDNA of a particular gene or one of the members of a cDNA library. The donor DNA may also be a genomic DNA that contains the coding region interrupted with non-coding sequences.

In another aspect, the present invention also provides a library of double-stranded circular donor DNAs that may be used for high throughput screening. The library of double-stranded circular DNA comprises: a donor DNA sequence which varies within a library of donor DNA sequences; a donor recombination site; and at least one selectable marker, the circular donor DNA not including an origin of replication.

The library of donor DNA sequences may be a library of cDNA or genomic DNA derived from any desirable sources. For example, the library of donor DNA sequences may be a cDNA library from single human chromosomes.

The circular donor DNA may further comprise a promoter sequence that controls expression of the donor DNA sequence. The promoter may be any array of DNA sequences that interact specifically with cellular transcription factors to regulate transcription of the downstream gene. The promoter may be derived from any organism, such as bacteria, yeast, insect and mammalian cells and viruses. Examples of the promoter include, but are not limited to, $E.$ $coli$ lac and trp operons, the tac promoter, the bacteriophage $\lambda \beta^L$ promoter, bacteriophage T7 and SP6 promoters, β-actin promoter, insulin promoter, human cytomegalovirus (CMV) promoter, HIV-LTR (HIV-long terminal repeat), Rous sarcoma virus RSV-LTR, simian virus SV40 promoter, baculoviral polyhedrin and p10 promoter.

The promoter may also be an inducible promoter that regulates the expression of downstream gene in a controlled manner. Examples of inducible promoters include, but are not limited to, the bacterial dual promoter (activator/repressor expression system) which regulates gene expression in mammalian cells under the control of tetracycline and its analogs and promoters that regulate gene expression under the control of factors such as heat shocks, steroid hormones, heavy metals, phorbol ester, the adenovirus E1A element, interferon, or serum.

The donor recombination site may be any segment or arrays of DNA sequence recognized by a site-specific recombinase which catalyzes site-specific fusion between the circular donor DNA and an acceptor vector. The site-specific recombinase may be a recombinase, a transposase or an integrases.

In one variation, the recombination site is a lox site that is recognized by the Cre recombinase of bacteriophage PI. Example of lox site includes, but are not limited to, loxB, loxL, loxR, loxP [SEQ ID NO:1], loxP3, loxP23, loxΔ86, loxΔ117, loxP511 [SEQ ID NO:2], and loxC2 [SEQ ID NO:3].

In another variation, the recombination site is a recombination site that is recognized by a recombinases other than Cre. Examples of the non-Cre recombinases include, but are not limited to, site-specific recombinases include: att sites recognized by the Int recombinase of bacteriophage λ (e.g. att1, att2, att3, attP, attB, attL, and attR), the FRT sites recognized by FLP recombinase of the 2pi plasmid of $Saccharomyces\ cerevisiae$, the recombination sites recognized by the resolvase family, and the recombination site recognized by transposase of $Bacillus\ thruingiensis.$ The example of site-specific recombinase include, but are not limited to, bacteriophage P1 Cre recombinase, yeast FLP recombinase, Inti integrase, bacteriophage λ, phi 80, P22, P2, 186, and P4 recombinase, Tn3 resolvase, the Hin recombinase, and the Cin recombinase, $E.\ coli$ xerC and xerD recombinases, $Bacillus\ thuringiensis$ recombinase, Tpnl and the β-lactamase transposons, and the immunoglobulin recombinases, The selectable marker of the circular donor DNA may be any functional element for facilitating subsequent identification and selection of clones of the recombination product under suitable conditions. The selectable marker may encode any functional element, such as protein, peptide, RNA, binding site for RNA and proteins, or products that provide resistance to organic or inorganic agents. Examples of selectable markers include, but are not limited to, reporter genes such as -galactosidase (GAL), fluorescent proteins (e.g., GFP, GFP-UV, EFFP, BFP, EBFP, ECFP, EYFP), secreted form of human placental alkaline phosphatase (SEAP), β-glucuronidase (GUS)); resistance genes against antibiotics (e.g. neomycin (G418) or hygromycin resistant gene, puromycin resistant gene), yeast seletable markers leu2-d and URA3, apoptosis resistant genes (e.g. baculoviral p35 gene), and antisenoligonucleotides.

The circular donor DNA may optionally include an affinity tag for selection and isolation of protein product encoded by the donor DNA segment. Examples of such an affinity tag include, but are not limited to, a polyhistidine tract, polyarginine, glutathione-S-transferase (GST), maltose binding protein (MBP), a portion of staphylococcal protein A (SPA), and various immunoaffinity tags (e.g. protein A) and epitope tags such as those recognized by the EE (Glu-Glu) antipeptide antibodies. The affinity tag may be positioned at either the amino- or carboxy-terminus of the donor DNA.

The present invention also provides a circular acceptor vector for generating recombinant expression vector. The vector comprises an origin of replication; and an acceptor recombination site capable of recombining with a donor DNA. Optionally, the acceptor vector may not include a promoter for regulating expression of the donor DNA.

The circular acceptor vector may be any vector that can transform, transfect or transduce a host cell. The acceptor vector may be a plasmid, a phage or a viral vector as long as it is able to replicate in vitro or in a host cell, or to convey the donor DNA to a desired location within a host cell. Examples of host cells include, but are not limited to, bacterial (e.g. $E.\ coli,\ Bacillus\ subtilis,$ etc.), yeast, animal, plant, and insect cells.

In one variation, the circular acceptor vector may be a prokaryotic plasmid. Optionally, the acceptor vector may comprise a prokaryotic termination sequence. Examples of the prokaryotic termination sequence include, but are not limited to, the T7 termination sequence, the $T_{INT}$, $T_{L1}$, $T_{L2}$, $T_{L3}$, $TR_1$, $TR_2$, $T_{6S}$ termination signals derived from the bacteriophage λ.

In another variation, the circular acceptor vector may be a mammalian expression vector. The mammalian expression vector contains one or more eukaryotic marker genes, appropriate eukaryotic transcriptional and translational termination signals and a sequence that signals polyadenylation of the transcript messenger RNA (mRNA), and an origin of replication that functions in a mammalian host cell. Examples of the eukaryotic polyadenylation sequence include, but are not limited to, the Herpes simplex virus thymidine kinase polyadenylation sequence, the bovine growth hormone polyadenylation sequence, and the simian virus 40 polyadenylation sequence.

Optionally, the eukaryotic expression vector may also carry an origin of replication and selectable marker genes that function in bacterial cells, forming a shuttle vector.

In yet another variation the circular acceptor includes a promoter for regulating expression of the donor DNA sequence carried by a circular donor DNA of the invention. According to this variation, the recombination site may be placed downstream of the promoter and the transcription initiation site in the acceptor vector.

In yet another variation, the circular acceptor may be a yeast expression vector such as a *S. cerevisiae* expression vector. Various types of *S. cerevisiae* expression vector include, but are not limited to, episomal or plasmid vector, integrating vectors, and yeast chromosomes (YACs).

In yet another variation, the circular acceptor vector may be a baculovirus DNA, such as wild type or mutant genomes of *Autographa californica* multiple nuclear polyhedrosis virus (AcMNPV).

Optionally, a baculoviral acceptor vector according to the present invention may not contain a polyhedrin promoter. Instead, the polyhedrin or the baculoviral p10 promoter can be positioned upstream of the donor DNA sequence of the circular donor DNA of the present invention.

The present invention also provides kits for generating recombinant vectors. In one embodiment, the kit comprises: a double-stranded circular donor DNA comprising a donor DNA sequence, a donor recombination site, and at least one selectable marker, the circular donor DNA not including an origin of replication; and a circular acceptor vector comprising an origin of replication and an acceptor recombination site capable of recombining with the circular donor DNA.

In another embodiment, the kit comprises: a library of double-stranded circular donor DNA comprising a donor DNA sequence which varies within a library of donor DNA sequences, a donor recombination site, and at least one selectable marker, the circular donor DNA not including an origin of replication; and a circular acceptor vector comprising an origin of replication and an acceptor recombination site capable of recombining with the circular donor DNA.

In yet another embodiment, the kit comprises: one or more linear donor DNA comprising a donor DNA sequence; a linear driver DNA comprising a promoter sequence, a recombination site, and at least one selectable marker, ligation of the linear donor DNA and the linear driver DNA resulting in a circular donor DNA; and a circular acceptor vector comprising an origin of replication and an acceptor recombination site capable of recombining with the circular donor DNA.

The present invention also provides a method for generating recombinant expression vector in vitro through site-specific recombination between a circular donor DNA and circular acceptor DNA, each containing recombination site recognized by the recombinase. The method comprises: contacting a circular double-stranded donor DNA and a circular acceptor vector in the presence of a recombinase under conditions suitable for the circular double-stranded donor DNA and circular acceptor vector to recombine to form a single fused circular vector. In this method, the circular double-stranded donor DNA comprises a donor DNA sequence, a donor recombination site, and at least one selectable marker, but not including an origin of replication. The circular acceptor vector comprises an origin of replication and an acceptor recombination site capable of recombining with the circular donor DNA. The promoter for regulating expression of the donor DNA may be contained in either the donor DNA or acceptor vector.

According to this method, the circular donor DNA containing a site-specific recombination site may be recombined with a circular acceptor vector in the presence of Cre recombinase. The recombination sites on the circular donor DNA and the circular acceptor vector may each contain a lox site.

The method may further include steps of transforming, transfecting or transducing a host cell and selecting the correctly fused recombinant vector based on the selectable phenotype conferred by the selectable marker gene on the recombinant vector.

The present invention also provides a method for generating recombinant expression vectors from linear DNA segments in vitro. The method comprises: ligating one or more double-stranded linear donor DNA which includes a donor DNA sequence with a double-stranded linear driver DNA which includes a promoter sequence and a donor recombination site to form a single circular donor DNA, the singular circular donor DNA not including an origin of replication, where the donor DNA sequence is under the transcriptional control of the promoter; and contacting the circular donor DNA and a circular acceptor acceptor vector in the presence of a recombinase to form a single fused circular vector. In this method, the circular acceptor vector comprises an origin of replication and an acceptor recombination site capable of recombining with the circular donor DNA.

According to this method, the linear donor DNA and linear driver DNA may contain matching restriction sites or other type of annealing sites so as to be ligated to form a circulaized DNA. The linear donor and driver DNAs may be derived from PCR amplification products.

The present invention also provides a method for high throughput production of recombinant expression vectors from linear DNA segments in vitro. The method comprises: ligating a library of double-stranded linear donor DNAs, where each member of the library includes a donor DNA sequence, with a double-stranded linear driver DNA which includes a promoter sequence and a donor recombination site to form a single circular donor DNA, the singular circular donor DNA not including an origin of replication, where the donor DNA sequence is under the transcriptional control of the promoter; and contacting the circular donor DNA and a circular acceptor acceptor vector in the presence of a recombinase to form a single fused circular vector. In this method, the circular acceptor vector comprises an origin of replication and an acceptor recombination site capable of recombining with the circular donor DNA.

According to this method, the library of double-stranded linear donor DNAs may be DNAs amplified from a library of cDNA clones. The library of cDNA clones may be arrayed in a multi-well plate such as 96- and 384-well plates. The library of cDNA clones may be a cosmid or phage library.

Also according to the method, ligating the library of double-stranded linear donor DNAs with a double-stranded linear driver DNA may be performed by Ligation Independent Cloning (LIC). Alternatively, ligating the library of double-stranded linear donor DNAs with a double-stranded linear driver DNA may be performed in the presence of T4 DNA ligase.

The method may further include a step of transferring the recombinant expression vector into a host and isolating the protein expressed from the vector by affinity tagging. The affinity tagging may be based on a polyhistidine tag (e.g. $His_6$), a protein tag (e.g., GST, maltose binding protein) or an epitope tag (e.g. an EE ag).

The methods of the present invention allow rapid and efficient generation of expression vectors containing the gene of interest without bacterial cloning. Direct ligation of linear donor DNA and linear driver DNA to generate a circular donor DNA allows for efficient cloning of donor DNA such as a cDNA library into an expression vector in an automated and high throughput manner. The methods can be used in a wide variety of high throughput arrays for functional genomics, protein genomics (proteomics), and other human genome projects.

DETAILED DESCRIPTION OF THE INVENTION

Figure 1:
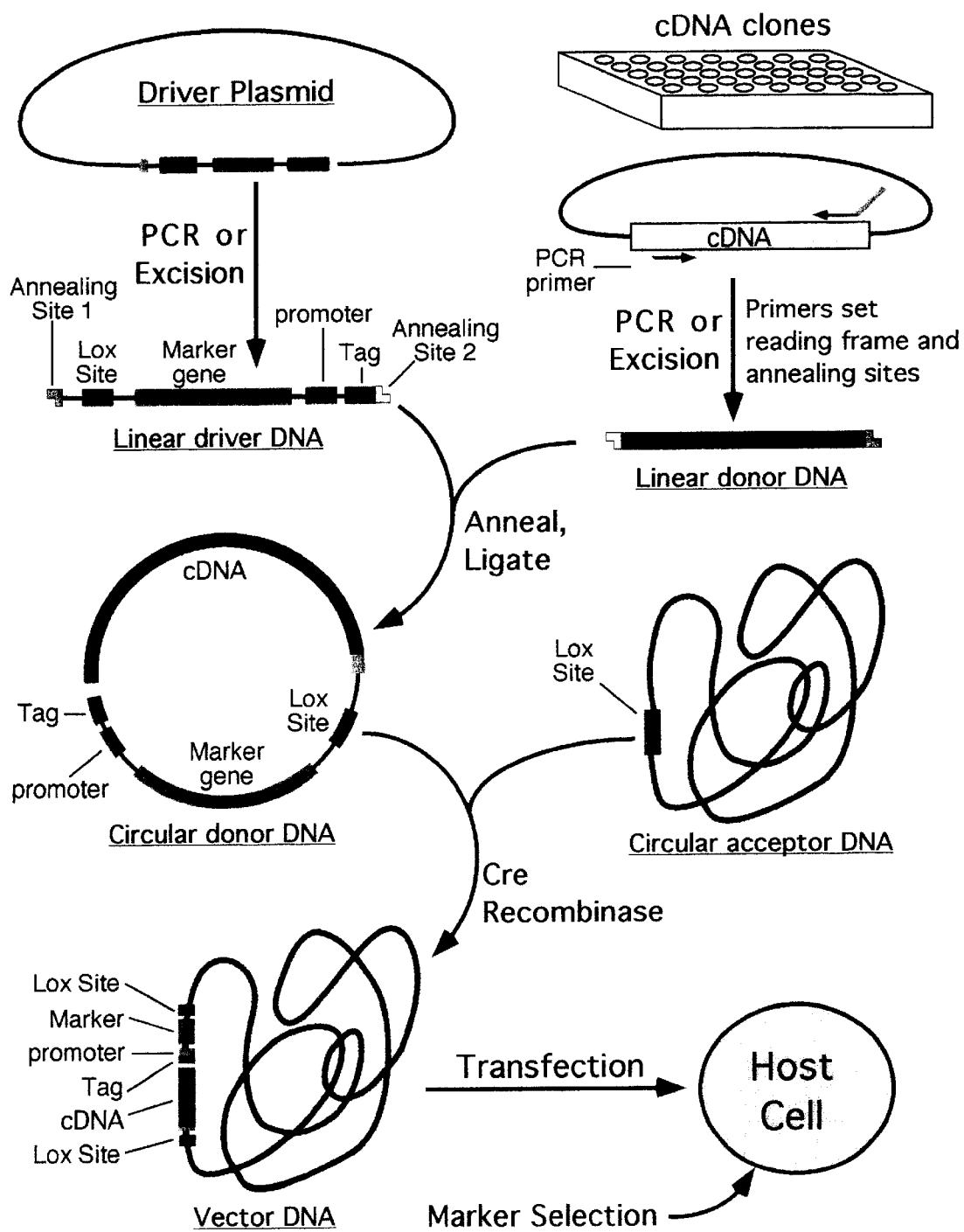
FIG. 1 illustrates a process of constructing a library of baculoviral expression vectors through Cre-mediated site-specific recombination.

The present invention provides reagents, kits and methods for use in a recombinational cloning or subdloning process, and, in particular, for -constructing expression vectors by using a site-specific recombinase in vitro or in vivo. In one aspect, a method is used to directly fuse a linear segment of donor DNA (e.g., gene of interest) with another linear segment of DNA comprising various functional elements such as promoters, selectable markers and a recombination site, resulting in a single circular donor DNA. This circular donor DNA is then recombined into a circular acceptor vector which also contains a recombination site through site-specific recombination catalyzed by a recombinase. The recombination product can be used to transform, transfect or transduce various types of host cells, depending on the specific type of acceptor vector used.

The circular donor DNA need not carry an origin of replication for propagation in host cells such as bacterial cells. Instead, the circular donor DNA may be produced from directly ligating two or more linear segments of DNA which may be amplified by polymerase chain reaction (PCR). Such a separation and ligation of different segments of DNA allows flexible distribution of different elements among the linear segments. For example, one linear segment may contain the gene of interest amplified from a cDNA library, while the other linear segment contains functional elements essential for subsequent recombination in vitro (or in vivo) and expression in host cells. By using a site-specific recombinase, such as Cre recombinase, this circular DNA can be recombined into any gene-transferring vector without using restriction enzymes as long as the vector carries a recombination site recognized by the recombinase. Further, direct ligation of linear segments of DNA avoids laborious steps of bacterial cloning and facilitates high throughput screening of large library of genetic materials, such as cDNA libraries derived from diseased tissues or cells. In addition, the circular DNA produced by direct ligation of these segments can be free of other undesirable genetic materials such as "junk DNA" derived from a bacterial plasmid that may affect expression, viability or stability of the recombinant vector.

1. Circular Donor DNA

The present invention provides a double-stranded circular donor DNA for transferring a donor DNA sequence into expression vectors. The circular donor DNA comprises: a donor DNA sequence; a donor recombination site; at least one selectable marker, the circular donor DNA not including an origin of replication. The donor DNA sequence may be any gene of interest which is needed to be transferred into an expression vector.

The present invention also provides a library of double-stranded circular donor DNAs which comprises: a donor DNA sequence which varies within a library of donor DNA sequences; a donor recombination site; and at least one selectable marker, the circular donor DNA not including an origin of replication.

The circular donor DNA contains a donor DNA segment (either cDNA or genomic DNA), a promoter (e.g. SV40 early gene enhancer), a selectable marker (e.g. Neo gene), and a sequence-specific recombinase target site (e.g. a loxP site). The promoter controls expression of the gene of interest and the selectable marker gene when the circular donor DNA is recombined with an acceptor vector and the resulting recombinant vector is introduced into a host cell. The circular donor DNA may further contain a polyadenylation signal for expression in mammalian cells.

The donor DNA sequence may be any deoxyribonucleotide sequence aencoding a functional gene or any synthetically generated DNA sequence. For example the donor DNA segment may be a sequence derived from cDNA of a particular gene or one of the members of a cDNA library. The cDNA library may be produced by converting mRNAs in a sample into double-stranded complementary DNA (cDNA) by using reverse transcriptase (RT) and the Klenow fragment of nucleic acid polymerase I. Depending on the source of mRNA sample, the cDNA library may contain various populations of genes of interest, such as disease genes located in certain tissue or type of cells. The donor DNA may also be a genomic DNA that contains the coding region interrupted with non-coding sequences (introns/intervening sequences). These introns may contain regulatory elements such as enhancers.

The circular donor DNA may further comprises a promoter sequence that controls expression of the donor DNA sequence. The promoter may be any array of DNA sequences that interact specifically with cellular transcription factors to regulate transcription of the downstream gene. The promoter may be derived from any organism, such as bacteria, yeast, insect and mammalian cells and viruses. The selection of a particular promoter depends on what cell type is to be used to express the protein of interest. Examples of the promoter include, but are not limited to, *E. coli* lac and trp operons, the tac promoter, the bacteriophage $\lambda \beta P^L$ promoter, bacteriophage T7 and SP6 promoters, β-actin promoter, insulin promoter, human cytomegalovirus (CMV) promoter, HIV-LTR (HIV-long terminal repeat), Rous sarcoma virus RSV-LTR, simian virus SV40 promoter, baculoviral polyhedrin and p10 promoter. The promoter may also be an inducible promoter that regulates the expression of downstream gene in a controlled manner, such as under a specific condition of the cell culture. Examples of inducible promoters include, but are not limited to, the bacterial dual promoter (activator/repressor expression system) which regulates gene expression in mammalian cells under the control of tetracyclines (Gossen, M. and Bujard, H. 1992, Proc.Natl. Acad. Sci. USA, 89, 5547–5551) and promoters that regulate gene expression under the control of factors such as heat shocks, steroid hormones, heavy metals, phorbol ester, the adenovirus E1A element, interferon, or serum.

The recombination site may be any segment or arrays of DNA sequence recognized by site-specific recombinase which catalyzes site-specific fusion between the circular donor DNA and the acceptor vector. The site-specific recombinase may be any enzymes that recognize short DNA sequences that become the crossover regions during the recombination event, including but not limited to recombinases, transposases and integrases.

Site-specific recombinases may derived from prokaryotic and eukaryotic sources. Examples of site-specific recombination include 1) chromosomal rearrangements which occur in *Salmonella typhimurium* during phase variation, inversion of the FLP sequence during the replication of the yeast 2 μ circle and in the rearrangement of immunoglobulin and T cell receptor genes in vertebrates, 2) integration of bacteriophages into the chromosome of prokaryotic host cells to form a lysogen and 3) transposition of mobile genetic elements (e.g., transposons) in both prokaryotes and eukaryotes.

In one embodiment, the recombination site is a loxP site that is recognized by the Cre recombinase of bacteriophage PI. The Cre recombinase catalyzes recombination of DNA between two loxP sites. The loxP site consists of a double-stranded 34 bp sequence:

5'-ATAACTTCGTATAATGTATGCTATACGMGTTAT-3'

3'-TATTGAAGCATATTACATACGATATGCTTCAATA-5' (SEQ ID NO:1)

The loxP site comprises two 13 bp inverted repeat sequences separated by an 8 bp spacer region. Hoess et al. (1982) Proc. Natl. Acad. Sci. USA 79:3398. The internal spacer sequence of the loxP site is asymmetrical and thus, two loxP sites can exhibit directionality relative to one another. Hoess et al. (1984) Proc. Natl. Acad. Sci. USA 81:1026. When two loxP sites on the same DNA molecule are in a directly repeated orientation, Cre excises the DNA between these two sites leaving a single loxP site on the DNA molecule. Abremski et al. (1983) Cell 32:1301. If two loxP sites are in opposite orientation on a single DNA molecule, Cre inverts the DNA sequence between these two sites rather than removing the sequence.

The Cre recombinase also recognizes a number of variant or mutant lox sites relative to the loxP sequence. Examples of these Cre recombination sites include, but are not limited to, the loxB, loxL and loxR sites which are found in the *E. coli* chromosome. Hoess et al. (1982), supra. Other variant lox sites include:

loxP511 site: 5'-ATAACTTCGTATAGTATACATTATACGAAGTTAT-3' (SEQ ID NO:2);

Hoess et al. (1986) Nucleic Acid Res. 14:2287–2300, loxC2 site: 5'-ACAACTTCGTATAATGTATGCTATACGAAGTTAT-3' (SEQ ID NO:3)

U.S. Pat. No. 4,959,317.

Cre catalyzes the cleavage of the lox site within the spacer region and creates a six base-pair staggered cut. Hoess and Abremski (1985) J. Mol. Biol. 181:351. The two 13 bp inverted repeat domains of the lox site represent binding sites for the Cre protein. If two lox sites differ in their spacer regions in such a manner that the overhanging ends of the cleaved DNA cannot reanneal with one another, Cre may not efficiently catalyze a recombination event using the two different lox sites. For example, it has been reported that Cre could not efficiently recombine a loxP site and a loxP511 site; these two lox sites differ in the spacer region. Two lox sites which differ due to variations in the binding sites (i.e., the 13 bp inverted repeats) may be recombined by Cre provided that Cre can bind to each of the variant binding sites; the efficiency of the reaction between two different lox sites (varying in the binding sites) may be less efficient that between two lox sites having the same sequence (the efficiency will depend on the degree and the location of the variations in the binding sites). For example, the loxC2 site can be efficiently recombined with the loxP site; these two lox sites differ by a single nucleotide in the left binding site.

The Cre protein has been purified to homogeneity. Abremski et al. (1984) J. Mol. Biol. 259:1509. And the cre gene has been cloned and expressed in a variety of host cells. Abremski et al. (1983), supra. Purified Cre protein is available from a number of suppliers (e.g., Novagen and New England Nuclear/Du Pont).

The recombination site of the circular DNA may also be selected from a variety of other recombination sites recognized by recombinases other than Cre. Examples of the non-Cre recombinases include, but are not limited to, site-specific recombinases include: the Int recombinase of bacteriophage, the FLP recombinase of the 2pi plasmid of *Saccharomyces cerevisiae*, the resolvase family, transposase of *Bacillus thruingiensis*.

The Int recombinase of bacteriophage λ belongs to the integrase family and mediates the integration of the λ genome into the *E. coli* chromosome. The Int recombinase of bacteriophage λ promotes irreversible recombination between its substrate att sites as part of the the formation or induction of a lysogenic state. Landy, A., (1989) Ann. Rev. Biochem. 58:913. Reversibility of the recombination reactions results from two independent pathways for integrative and excisive recombination. Each pathway uses a unique but overlapping set of the 15 protein binding sites that comprise aft site DNAs. Cooperative and competitive interactions involving four proteins (Int, Xis, IHF and FIS) determine the direction of recombination. Integrative recombination involves the Int and IHF proteins and sites attP (240 bp) and attB (25 bp). Recombination results in the formation of two new sites: attL and attR. Excisive recombination requires Int, IHF, and Xis, and sites attL and attR to generate attP and aftB. Under certain conditions, FIS stimulates excisive recombination. In addition to these normal reactions, it should be appreciated that attP and attB, when placed on the same molecule, can promote excisive recombination to generate two excision products, one with attL and one with attR. Similarly, intermolecular recombination between molecules containing attL and attR, in the presence of Int, IHF and Xis, can result in integrative recombination and the generation attP and attB. Derivatives of the att site with changes within the 15 bp core may also be suitable for efficient recombination. By incorporating a native or modified att site in both the circular donor DNA and the acceptor vector, intermolecular recombination between the donor and acceptor DNA molecules may be achieved by using the appropriate recombination protein such as Int, IHF and FIS, with or without Xis. Integrase can be obtained as described by Nash, H. A., (1983) Methods of Enzymology 100:210–216. IHF can be obtained as described by Filutowicz, M., et al., (1994) Gene 147:149–150.

The other members of the integrase family of site-specific recombinases may also be used to provide alternative recombination proteins and recombination sites for the present invention. Examples of such Int recombinases include, but not limited to, site-specific recombinase encoded by bacteriophage λ, phi 80, P22, P2, 186, P4. This group of recombinases exhibits a large diversity of sequences, but all of the recombinases can be aligned in their C-terminal halves. A 40-residue region near the C terminus is particularly well conserved in all the proteins and is homologous to a region near the C terminus of the yeast 2 μ plasmid Flp protein. Three positions are perfectly conserved within this family: histidine, arginine and tyrosine are found at respective alignment positions 396, 399 and 433 within the well-conserved C-terminal region. These residues contribute to the active site of this family of recombinases, and suggest that tyrosine-433 forms a transient covalent linkage to DNA during strand cleavage and rejoining. Argos, P. et al., (1986) EMBO J. 5:433–40.

The FLP recombinase of the 2pi plasmid of *Saccharomyces cerevisiae* recognizes the frt site which, like the loxP site, comprises two 13 bp inverted repeats separated by an 8 bp spacer:

5'-GAAGTTCCTATTCTCTAGAAAGT
ATAGGAACTTC-3' (SEQ ID NO:4)

Cox (1983) Proc. Natl. Acad. Sci. USA 80:4223. The FLP gene has been cloned and expressed in *E. coli* and in mammalian cells and has been purified. Meyer-Lean et al. (1987) Nucleic Acids Res. 15:6469; Babineau et al (1985) J. Biol. Chem. 260:12313; Gronostajski and Sadowski (1985) J. Biol. Chem. 260:12328.

The resolvase family members, such as the Tn3 resolvase, the Hin recombinase, and the Cin recombinase, may also be used for recombination between the circular donor DNA and the circular acceptor DNA. Although members of this highly related family of recombinases are typically constrained to intramolecular reactions (e.g., inversions and excisions) and can require host-encoded factors. Mutants have been isolated that relieve some of the requirements for host factors as well as some of the constraints of intramolecular recombination. Maeser and Kahnmann (1991) Mol. Gen. Genet. 230:170–176.

Transposase of *Bacillus thuringiensis* may also be used as recombination proteins and recombination sites. *Bacillus thuringiensis* is an entomopathogenic bacterium whose toxicity is due to the presence in the sporangia of A-endotoxin crystals active against agricultural pests and vectors of human and animal diseases. Most of the genes coding for these toxin proteins are plasmid-borne and are generally structurally associated with insertion sequences (IS231, IS232, IS240, ISBT1 and ISBT2) and transposons (Tn4430 and Tn5401). Several of these mobile elements have been shown to be active and participate in the crystal gene mobility, thereby contributing to the variation of bacterial toxicity. Structural analysis of the iso-IS231 elements indicates that they are related to IS1151 from *Clostridium perfringens* and distantly related to IS4 and IS186 from *E. coli*. Like the other IS4 family members, they contain a conserved transposase-integrase motif found in other IS families and retroviruses. Functional data gathered from IS231A in *E. coli* indicate a non-replicative mode of transposition, with a preference for specific targets. Similar results were also obtained in *Bacillus subtilis* and *B. thuringiensis*. Mahillon, J. et al., (1994) Genetica 93:13–26; (1992) Campbell, J. Bacteriol. 7495–7499.

Other recombination systems may also be used as recombination proteins and recombination sites, including the xerC and xerD recombinases of *E. coli* which together form a recombinase that recognizes the 28 bp dif site (Leslie and Sherratt (1995) EMBO J. 14:1561); the Int protein from the conjugative transposon Tn916 (Lu and Churchward (1994) EMBO J. 13:1541); Tpnl and the β-lactamase transposons (Levesque (1990) J. Bacteriol. 172:3745); and the immunoglobulin recombinases (Malynn et al. (1988) Cell 54:453).

Other than the wild-type recombination sites, modified recombination sites may also be used in the present invention. Wild-type recombination sites may contain sequences that reduce the efficiency or specificity of recombination reactions. For example, multiple stop codons in attB, attR, attp, attL and loxP recombination sites occur in multiple reading frames on both strands, thereby reducing recombination efficiencies. For example att sites, such as att1, att2, and att3 sites, may be modified to have one or multiple mutations to enhance specificity or efficiency of the recombination reaction and to decrease reverse reaction by removing P1 and H1 from attB.

The circular donor DNA also contains one or more selectable markers to facilitate subsequent identification and selection of clones of the recombination product under suitable conditions. The selectable marker may encode any functional element, such as protein, peptide, RNA, binding site for RNA and proteins, or products that provide resistance to organic or inorganic agents. Examples of selectable markers include, but are not limited to, reporter genes such as P-galactosidase (GAL), fluorescent proteins (e.g., GFP, GFP-UV, EFFP, BFP, EBFP, ECFP, EYFP), secreted form of human placental alkaline phosphatase (SEAP), β-glucuronidase (GUS)); resistance genes that encodes products which provide resistance against other wise toxic agents such as antibiotics (e.g. neomycin (G418) or hygromycin resistant gene, puromycin resistant gene), yeast seletable markers leu2-d and URA3, apoptosis resistant genes (e.g. the baculoviral p35 gene) that encode proteins that binds to products which are detrimental to cell survival and promote apoptosis; antisenoligonucleotides, and any other DNA that encodes product that directly or directly confer sensitivity of cells to particular agents.

The circular donor DNA may optionally include an affinity tag for selection and isolation of protein product encoded by the donor DNA segment. Examples of such an affinity tag include, but are not limited to, a polyhistidine tract, polyarginine, glutathione-S-transferase (GST), maltose binding protein (MBP), a portion of staphylococcal protein A (SPA), and various immunoaffinity tags (e.g. protein A) and epitope tags such as those recognized by the EE (Glu-Glu) antipeptide antibodies. Th affinity tag may also be a signal peptide either native or heterologous to baculovirus, such as honey bee mellitin signal peptide. The affinity tag may be positioned at either the amino- or carboxy-terminus of the donor DNA.

2. Circular Acceptor Vector

The present invention also provides a circular acceptor vector for generating recombinant expression vector. The vector comprises an origin of replication; and an acceptor recombination site capable of recombining with a donor DNA. Optionally, the acceptor vector may not include a promoter for regulating expression of the donor DNA.

The circular acceptor vector may be any vector that can transform, transfect or transduce a host cell. The acceptor vector comprises a recombination site which is recognized by a site-specific recombinase and recombined with a donor DNA carrying another recombination site. The acceptor vector may be plasmids, phages or viral vectors as long as it is able to replicate in vitro, or in a host cell, or to convey the donor DNA to a desired location within a host cell. Examples of host cells include, but are not limited to, bacterial (e.g. *E. coli, Bacillus subtilis*, etc.), yeast, animal, plant, and insect cells.

For plasmid-based expression vector, the recombination site may be introduced into the vector by a double-stranded oligonucleotide containing the desired site-specific recombination site (e.g., a lox site). The double-stranded oligonucleotide may be formed by annealing two synthetic single-stranded oligonuceotides to form two ends which are compatible with ends of a linearized plasmid vector. The matching ends may be generated by restriction enzyme digestion or by using cloning kits such as the TA cloning kits available from Invitrogen, Inc. (San Diego, Calif.).

The circular acceptor vector may be any prokaryotic plasmid that contains a recombination site (e.g. loxP site), a basic backbone of plasmid cloning vector such as pBR322, including one or more antibiotic resistant genes (e.g. Amp$^r$, Tet$^r$) and an origin of replication that function in specific host cells. After recombination between the circular donor DNA and the acceptor vector to form a fused plasmid, this plasmid vector can be used to transform bacterial cells. In the transformed cell, a prokaryotic promoter, either carried by the donor DNA or the acceptor vector, causes expression of the donor DNA under suitable conditions.

Optionally, the acceptor vector may comprise a prokaryotic termination sequence. Examples of the prokaryotic termination sequence include, but are not limited to, the T7 termination sequence. A variety of termination sequences are known to the art and may be employed in the nucleic acid constructs of the present invention including, the $T_{INT}$, $T_{L1}$, $T_{L2}$, $T_{L3}$, $TR_1$, $TR_2$, $T_{6S}$ termination signals derived from the bacteriophage Hendrix et al. Eds., Cold Spring Harbor Press, Cold Spring Harbor, N.Y. (1983) and termination signals derived from bacterial genes such as the trp gene of *E. coli*.

The circular acceptor vector may also be a mammalian expression vector that contains a recombination site (e.g. loxP site), one or more eukaryotic marker gene, the appropriate eukaryotic transcriptional and translational termination signals and a sequence that signals polyadenylation of the transcript messenger RNA (mRNA), and an orgin of replication that functions in a mammalian host cell. Examples of the eukaryotic polyadenylation sequence include, but are not limited to, the Herpes simplex virus thymidine kinase polyadenylation sequence, the bovine growth hormone polyadenylation sequence, and the simian virus 40 polyadenylation sequence.

If the circular acceptor carries a promoter for regulating expression of the donor DNA sequence, the recombination site may be placed downstream the promoter and transcription initiation site in acceptor vector. This modification of the vector may be easily accomplished using synthetic oligonucleotides comprising the desired recombination site (loxP site). In designing the oligonucleotide comprising the recombination site, it may be desirable to avoid introducing an ATG or start codon that might initiate translation inappropriately, or in-frame stop codons.

For expression vectors intended to generate a fusion protein between a protein domain located at the amino-terminus of the fusion protein and the protein encoded by the donor DNA, care may be taken to place the recombination site in the correct reading frame such that 1) an open reading frame is maintained through the recombination site on pHOST and 2) the reading frame in the recombination site on the acceptor vector is in frame with the reading frame found on the recombination site contained within the circular donor DNA.

Optionally, the eukaryotic expression vector may also carry an origin of replication and selectable marker genes that function in bacterial cells, forming a shuttle vector. After recombination between the circular donor DNA and the acceptor vector to form a fused expression vector, this vector can be used to transfect animal cells. In the transfected cell, a eukaryotic promoter, either carried by the donor DNA or the acceptor vector, causes expression of the donor DNA under suitable conditions.

The circular acceptor may also be a yeast expression vector such as a *S. cerevisiae* expression vector that includes a recombination site. Various types of *S. cerevisiae* expression vector include episomal or plasmid vector, integrating vectors, and yeast chromosomes (YACs). A YAC-based expression vector may be used to carry large segment of donor DNA, which is then maintained as a separate chromosome in the host yeast cell.

The circular acceptor vector may also be a baculovirus DNA (genome) that is modified to contain a recombination site (e.g. a loxP site). For example, the baculoviral genome of *Autographa californica* multiple nuclear polyhedrosis virus (AcMNPV) may be modified to include a site-specific recombination site, such as a loxP site. *A. californica* (the alfalfa loop) and over 30 other insect species can be infected by AcMNPV. This virus also grows well on many insect cell lines, such as Sf cell lines derived from the fall armyworm, *Spodoptera frugiperda*. In these cells, the the promoter of the viral protein, polyhedrin, is exceptionally strong when the virus infects the cell. Such polyhedrin promoter can promote high level expression of downstream foreign gene that replaces the polyhedrin gene.

The recombination site (e.g. a loxP site) may be introduced into a baculoviral vector through homologous recombination in vivo. For example, a baculoviral transfer vector may be used to shuttle the loxP site into the wild type baculoviral DNA (e.g. AcMNPV) to form the final circular baculoviral vector. An example of such transfer vector is the p36C that contains baculoviral polyhedrin flanking sequences, up- and down-stream AcMNPV DNAs for homologous recombination. Page (1989) Nucleic Acids Res. 17: 454. The lopP site may be introduced into the transfer vector by regular oligonucleotide-mediated mutagenesis. A portion of the polyhedrin flanking sequence is replaced with the loxP site using an oligonucleotide containing the loxP site. The the resulting loxP-containing transfer vector and the wild type baculoviral DNA are co-transfected into insect cells such as Sf9 cells. Because the transfer vector contains the polyhedrin flanking sequences, a double crossover homologous recombination occurs in the cells, causing the replacement of the polyhedrin gene in AcMNPV DNA with the loxP site and therefore resulting in the integration of the loxP site into the AcMNPV genome. After a desired period of time (e.g. 72 hr) the supernatant of the insect cell culture is harvested and the progeny virus is screened in a standard agarose overlay assay. Brown and Faulkner (1977) J. Gen. Virol. 36: 361–364. Polyhedrin-negative plaques are purified to homogenity by successive rounds of agarose overlay assay. The presence of the loxP site may be confirmed by Southern analysis of DNA from the infected cells.

Optionally, the baculoviral acceptor vector according to the present invention may not contain the polyhedrin promoter. Instead, the polyhedrin promote or a baculoviral p10 promoter is positioned upstream of the donor DNA sequence of the circular donor DNA. After site-specific recombination between the circular donor DNA and a baculoviral acceptor vector, the resulting recombinant baculoviral vector can be used to infect insect cells, such as Sf9 cells.

Also optionally, the circular acceptor vector according to the present invention may include a negatively selectable marker gene, such as the selectable marker based on herpes simplex virus tk gene or any kind of gene encoding a protein that signals apoptosis and causes programmed cell death, such as the CAR1 gene. Expression of these negatively selectable marker genes results in cell death, thereby eliminating those cells containing the circular acceptor vector that does not recombine with the circular donor DNA.

The present invention also provides kits for generating recombinant vectors. In one embodiment, the kit comprises: a double-stranded circular donor DNA comprising a donor DNA sequence, a donor recombination site, and at least one selectable marker, the circular donor DNA not including an origin of replication; and a circular acceptor vector comprising an origin of replication and an acceptor recombination site capable of recombining with the circular donor DNA.

In another embodiment the kit comprises: a library of double-stranded circular donor DNA comprising a donor DNA sequence which varies within a library of donor DNA sequences, a donor recombination site, and at least one selectable marker, the circular donor DNA not including an origin of replication; and a circular acceptor vector comprising an origin of replication and an acceptor recombination site capable of recombining with the circular donor DNA.

In yet another embodiment, the kit comprises: one or more linear donor DNA comprising a donor DNA sequence; a linear driver DNA comprising a promoter sequence, a recombination site, and at least one selectable marker, ligation of the linear donor DNA and the linear driver DNA resulting in a circular donor DNA; and a circular acceptor vector comprising an origin of replication and an acceptor recombination site capable of recombining with the circular donor DNA.

3. Method of Generating Recombinant Expression Vectors through Site-Specific Recombination The present invention provides a method for generating recombinant expression vector in vitro through site-specific recombination between a circular donor DNA and circular acceptor DNA, each containing recombination site recognized by the recombinase. The method comprises: contacting a circular double-stranded donor DNA and a circular acceptor vector in the presence of a recombinase under conditions suitable for the circular double-stranded donor DNA and circular acceptor vector to recombine to form a single fused circular vector.

In this method, the circular double-stranded donor DNA comprises a donor DNA sequence, a donor recombination site, and at least one selectable marker, but not including an origin of replication. The circular acceptor vector comprises an origin of replication and an acceptor recombination site capable of recombining with the circular donor DNA. The promoter for regulating expression of the donor DNA may be contained in either the donor DNA or acceptor vector.

According to this method, the circular donor DNA containing a site-specific recombination site can be recombined with a circular acceptor vector in the presence of a site-specific recombinase, such as Cre recombinase. In vitro Cre recombinase can catalyze fusion of the donor DNA into the acceptor vector which contains another copy of the recombination site (e.g. loxP site) found on the circular donor DNA. Optionally, the circular donor DNA may contain a promoter positioned upstream of the donor DNA sequence to regulate expression of the donor DNA once the recombinant vector is introduced into a host cell.

Alternatively, the promoter for regulating expression of the donor DNA sequence may be positioned upstream of the recombination site of the acceptor vector. Following the site-specific recombination between the recombination sites located on the donor DNA and acceptor vector, the two circular DNAs are stably fused in a manner that places the expression of the donor DNA sequence under the control of the promoter contained within the acceptor vector. The recombination occurs in a manner that retains the proper translational reading frame of the donor DNA.

Following the in vitro recombination, a portion of the reaction mixture may be used to transform, transfect or transduce a suitable host cell to permit the recovery and propagation of the recombinant expression vectors. The correctly fused recombinant vector may be selected for its ability to transform, transfect or transduce a host cell and express the selectable marker that is contained in the circular donor DNA and recombined into the acceptor vector. The selectable phenotype conferred by the selectable marker gene on the recombinant vector may be change of color of the host cells upon proper chemical treatment, secretion of protein in the culture that is detectable by colorometers or fluorometers, survival of cells under selection pressure or enhanced propagation of a virus such as baculovirus. The circular donor DNA cannot replicate in cells because it does not contain an origin of replication, and therefore, unless the circular donor DNA has integrated into the acceptor vector that contains an origin of expression, the circular donor DNA should not replicate in the host cell. The recombinant expression vector may be isolated from host cells which display the desired phenotype and verified by using various methods such as restriction enzyme digestion, sequencing and Southern blotting.

The present invention also provides a method for generating recombinant expression vectors from linear DNA segments in vitro. The method comprises: ligating one or more double-stranded linear donor DNA which includes a donor DNA sequence with a double-stranded linear driver DNA which includes a promoter sequence and a donor recombination site to form a single circular donor DNA, the singular circular donor DNA not including an origin of replication, where the donor DNA sequence is under the transcriptional control of the promoter; and contacting the circular donor DNA and a circular acceptor acceptor vector in the presence of a recombinase to form a single fused circular vector. In this method, the circular acceptor vector comprises an origin of replication and an acceptor recombination site capable of recombining with the circular donor DNA.

According to this method, the linear donor DNA and linear driver DNA may contain matching restriction sites or other type of annealing sites so as to be ligated to form a circulaized DNA. After the ligation, the circularized donor DNA contains a site-specific recombination site carried by the linear driver DNA. Such a circular donor DNA is recombined with a circular acceptor vector in the presence of a site-specific recombinase, such as Cre recombinase. The Cre recombinase can catalyze fusion of the donor DNA into the acceptor vector which contains another copy of the recombination site (e.g. loxP site) found on the circular donor DNA.

FIG. 1 illustrates a general scheme of this method according to the present invention. As illustrated in FIG. 1, a library of linear donor DNA (underlined) is directly ligated to a linear driver DNA (underlined) to generate a circular donor DNA. This allows for efficient cloning of donor DNA (e.g. cDNA library) into an expression vector in an automated and high throughput manner.

The linear donor and driver DNA can be generated by PCR amplification of a template DNA, either linear or contained in plasmids of cDNA clones. As illustrated in FIG. 1, a library of cDNA clones from a desired source may be rearrayed into 96-well plates by using a re-arraying robot. The library of cDNA clones may be cosmid and phage libraries that contain inserts primarily from single human chromosomes isolated by flow-sorting. These cDNA clones may be identified by their short sequence tags or expressed sequence tags (ESTs). These cDNA clones may be arrayed in multi-well microtiter plates such as 96- or 384-well plates and handled by robots. For each re-arrayed plate, data tracking system may be used to identify each clone, sequence accession number, passage number, etc.

The library of linear donor DNA may also be generated and amplified from total RNA or mRNA samples by using an RT-PCR method. The library of linear donor DNA can then be ligated with the linear driver DNA to form the circular donor DNA which is recombined with the circular acceptor. This allows direct transferring of the cDNA library (donor DNA) to the expression vector (acceptor vector) without going through a cloning step.

Alternatively, the library of linear donor DNA may be generated by random or site-directed mutagenesis of one or more target gene sequence. For example, "poisoned" PCR or DNA shuffling techniques may be used to generate a diverse library of donor DNA which can be incorporated into the circular donor DNA by using direct ligation according to the present invention. Clones of these mutagenized library can be screened for improved or unique biological functions in an appropriate expression system.

Bacterial cultures of the cDNA clones may be grown in the multi-well microtiter plates and directly used for PCR. Suitable PCR primers containing an annealing site may be used to amplify each cDNA clone in the plate. For example, PCR primers may be designed to hybridize to the sequence of the cDNA clones and contain sequences for Ligation Independent Cloning (LIC). High-fidelity thermostable polymerases are preferably used to reduce copying errors and numbers of amplification cycles. The PCR product, the linear cDNA library, may optionally be purified by passing through mini columns.

Similarly, the linear driver DNA may also be amplified by using primers containing a matching annealing site as the primers for amplifying donor DNA. The template of the driver DNA may also be a plasmid which contains functional elements, such as a site-specific recombination site, a promoter, a selectable marker gene, a tag, and a transcription termination signal.

Still referring to FIG. 1, the linear driver DNA is annealed and ligated with the linear donor DNA under suitable conditions in multiple-well plates (e.g. in the presence of T4 ligase). For ligation independent cloning (LIC), the linear driver DNA and the linear donor DNA generated by LIC PCR amplification are digested with T4 polymerase, annealed, and ligated together to form a library of circular donor DNAs (underlined).

The circular donor DNA may be mixed with a circular acceptor vector (underlined) containing a suitable recombination site (e.g. loxP) in the presence of a site-specific recombinase (e.g. Cre recombinase). For example, a circular baculoviral vector containing a loxP site may be mixed with an array of circular cDNA (circular donor DNA) in the presence of purified Cre recombinase or cell extract containing Cre. The amount of recombinase which is added to drive the recombination reaction between the donor and vector DNAs can be determined by using a titration assay is used to determine the appropriate amount of the purified recombinase enzyme or the appropriate amount of a Cre extract. The recombination reaction buffer compatible with purified Cre recombinase may contain 50 mM Tris-HCl (pH 7.5), 10 mM $MgCl_2$, 30 mM NaCl and 1 mg/ml BSA. The concentration of the circular donor DNA and the acceptor vector may vary between 10 ng to 10 μg of each vector per 20 μl reaction volume. The recombination reaction may be incubated at 37° C. for a necessary period of time and terminated by heating at 70° C. for 15 min.

Site-specific recombination between the donor cDNA array and the acceptor baculoviral vector in the presence of Cre recombinase results in a recombinant baculoviral vector (the vector DNA in FIG. 1). The recombinant baculoviral vector may be used to transfect Sf9 cells (the host cell in FIG. 1) arrayed in multi-well plates. The plates may be incubated at 27° C. for several days. The progeny baculovirus may be screened in an overlay assay of the supernatant. For example, the presence of the integrated donor DNA in the viral progeny may be determined by detecting level of expression of the selectable marker (e.g. β-GAL, GUS). Alternatively, a baculovirus apoptosis resistant gene (baculovirus p35 gene) may be used as a selectable marker to confer increased viral yield in certain incest cell lines. Clem et al. (1991) Science 254: 1388–1390. Recombinant baculovirus bearing this gene has been shown to be amplified up to a million folds in appropriate host cells. Lerch et al (1993) Nucleic Acid Res. 21: 1753–1760.

The protein product expressed by the recombinant expression vector may be seletively identified and purified by using affinity tagging. The tag element may be a short DNA sequence inserted between the promoter and the transcription termination sequence in a proper reading frame on the recombinant expression vector. Such a tag element may encodes a short amino acid sequence that specifically binds to a compound or a macromolecule. After transcription and translation of the recombinant expression vector in the host cells the short amino acid sequence which is part of the donor DNA construct, acts as an identification tag (affinity tag). In another word, the tag carried by the circular donor DNA that is recombined with the acceptor DNA is expressed as a fusion protein encoded by the donor DNA. The presence of the fusion protein can be identified through the affinity binding of the tag to its binding partner.

For example, a polyhistidine tag (e.g. $His_6$) may be used for isolating fusion proteins. The fusion protein carrying a His tag can be isolated by passing all proteins of a cell extract (e.g. Sf9 cells) through a column of Nitriacetic acid ararose beads. The unbound proteins are eluted from the column, and the bound fusion protein is selectively removed by either adding a competitor compound (e.g. imidazole) that dislodges the His tag of the fusion protein from the Ni ions or by lowing the pH of the elution buffer. If necessary, the tag may be removed form the fusion protein with a protease that cleaves only at the engineered site.

Alternatively, the affinity tag may be a protein tag (e.g., GST, maltose binding protein) or an epitope tag that are short amino acid sequences binding to glutathione, maltose and specific antibodies. For example, an antibody against an EE epitope tag may be used for identifying and purifying fusion protein encoded by the donor DNA. The EE (Glu-Glu) antipeptide antibody was raised against a peptide that contains the major tyrosine phosphorylation site of polyoma middle T antigen. Talmage et al. (1989) Cell 59: 55–56. The antibody has moderate affinity for the EE tag ($K_d$~$2\times10^{-7}$) which allows rapid elution of tagged fusion proteins by free peptide under non-denaturing conditions while retaining efficient binding of the fusion protein in crude lysates. Further, since the EE tag is a strong tyrosine kinase phosphorylation substrate for protein kinases (e.g. Src) it may serve as a detectation label for high throughput assays for protein interactions.

The methods of the present invention allow rapid and efficient generation of expression vectors containing the gene of interest without bacterial cloning. Various libaries of cDNA or genomic DNA that are difficult to be cloned in bacteria can be directly amplified and introduced into any expression vector. The methods can be used in a wide variety of high through arrays for functional genomics, protein genomics and other human genome projects. For example, the methods may be used for systematic functional analysis gene profiling, gene tagging, gene overexpression, or systematic transcript analysis. The information generated can shed light on functionally important pathways in diseased cells in many important areas such as oncology and inflammation. Further, the methods may be used for high-throughput genetic screens for target discovery and validation, as well as drug discovery based on the targets discovered in the screens.

EXAMPLE

Figure 2:
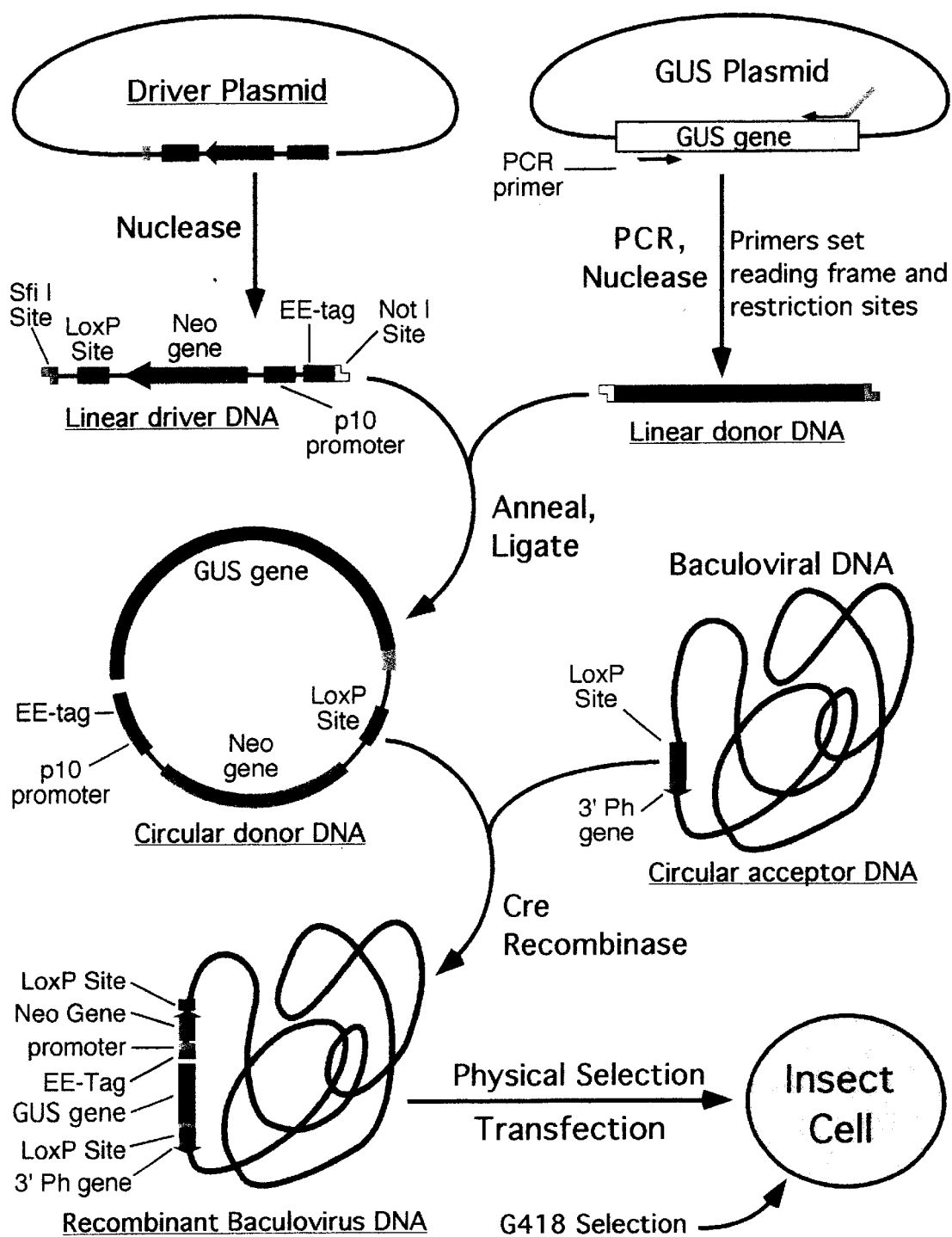
FIG. 2 illustrates a process of constructing a baculoviral expression vector for the GUS gene through Cre-mediated site-specific recombination.

FIG. 2 illustrates an example of how to construct a baculoviral expression vector for the GUS gene according to the present invention. As illustrated in FIG. 1, a recombinant baculoviral expression vector is generated in vitro without a cloning step. The following is a detailed elucidation of the steps of using the method.

1. Construction of the Driver Plasmid

A linear double-stranded driver DNA (underlined) is generated from a driver plasmid containing a baculoviral p10 promoter, a Neo marker gene, a loxP site and appropriate restrictions sites such as Sfi I and Not I sites. The Driver plasmid is constructed by using standard plasmid construction techniques as taught in Sambrook, et al. *Molecular Cloning: A laboratory Manual; DNA Cloning: A Practical Approach*, Vol I & II (D. Glover ed.); *Oligonucleotide Synthesis* (N. Giat, ed.). The driver plasmid is based on pBR322, a standard bacterial cloning vector plasmid, and the following elements are cloned into pBR322 contiguously, in the order shown below:

a) an SfiI restriction site (GGCCNNNNNGGCC) [SEQ ID NO: 6]
b) a loxP site (ATAACTTCGTATAATGTATGC TATACGAAGTTAT) [SEQ ID NO: 1]
c) a Neo gene with promoter and SV40 poly A addition site
d) a baculovirus p10 promoter
e) an EE-tag sequence (MEEEEYMPME) [SEQ ID NO: 5]
f) a NotI restriction site (GCGGCCGC) [SEQ ID NO:7]

Sequence of the baculoviral p10 promoter is described in Weyer U, Possee R D. (1989) J. Gen. Virol. 70:203–8 and is supplied by pAcAB4 from B D Pharmingen, San Diego, Calif. The sequence for the Neo gene with a promoter and SV40 poly A addition site is available from the plasmid pIE-neo supplied by Novagen Inc.

2. Amplification and Processing of the Donor Gene DNA

A linear double-stranded donor DNA (underlined) is amplified by PCR from a donor plasmid or a cDNA clone carrying the GUS gene. Oligonucleotide PCR primers that are homologous to the 5' and 3' ends of the GUS gene (source: pBacPAK8-GUS available from Clontech, Palo Alto, Calif.) are designed and synthesized. These primers also contain restriction sites (NotI for the 5' primer and SfiI for the 3' primer) in the 5' ends of the primers. The GUS gene is then amplified by PCR from the plasmid pBacPAK8-GUS containing the GUS gene using these primers.

The PCR products from GUS gene amplification are digested with NotI and SfiI restriction endonucleases to generate the appropriate sticky ends on the products, resulting in the linear double-stranded donor DNA.

3. Construction of the Circular Donor DNA

The driver plasmid described in Section 1 is digested with NotI and SfiI restriction endonucleases. The fragment which contains the elements listed above such as the loxP site and p10 promoter is isolated by gel electrophoresis purification, resulting in the linear double-stranded driver DNA.

The linear driver DNA is annealed to an excess of the linear donor DNA and ligated by using T4 DNA ligase to produce the circular donor DNA (underlined).

4. Construction of the Acceptor Baculovirus Genomic DNA

A baculovirus transfer vector plasmid containing a loxP site is constructed according to the protocol described by Peakman et al. (1992) nucleic Acid Res. 20:495–500. Briefly, a double-stranded oligonucleotide consisting of a loxP sequence [SEQ ID NO:1] with a blunt 5' end and a CTAG 5' overhang at the 3' end is synthesized. A baculovirus transfer vector pVL1392 (available from BD Pharmingen, San Diego, Calif.) is digested with EcoR V and BamH I restriction enzymes to remove the polyhedrin promoter in the vector. The double-stranded oligonucleotide with the loxP site is ligated with the EcoR V/BamH I digested plasmid pVL1392. The resulting ligated plasmid is transformed into bacteria and screened for colonies with the loxP insert. This generates a baculoviral transfer vector containing a loxP site.

The baculoviral transfer vector containing a loxP site is co-transfected with a linearized baculovirus DNA (BacPAK6 DNA from Clontech, Palo Alto, Calif.) by using standard baculovirus construction techniques (Methods in Molecular Biology Vol. 39: Baculovirus Expression Protocols, Christopher D. Ricardson ed., Humana Press, Totowa, N.J. 1995).

Recombinant baculovirus that contains the loxP site is isolated by plaque purification and baculoviral DNA is prepared from the virus to produce the circular acceptor DNA.

5. Recombination of the Circular Donor DNA and the Circular Acceptor DNA and Selection of the Recombinant Baculoviral DNA The circular acceptor DNA and the circular donor DNA generated as described above is recombined in the presence of GST-Cre recombinase (available from Invitrogen, San Diego, Calif.) by using the methods described by Liu et al. (1998) Current Biology 8:1300–1309. The mixture is then heated at 65° C. to inactivate the Cre recombinase.

The circular acceptor DNA that has recombined with the circular donor DNA is selected and purified from the recombination reaction mixture by using a method of "physical selection" described in Shepard & Rae (1997) Nucleic Acid Research 25:3183. Briefly, a biotinylated synthetic oligonucleotide probe that is substantially homologous to any region present in the circular donor DNA is used to hybridize with the recombined baculoviral DNA. The hybridized complex is then separated by using avidin-coated magnetic beads via biotin-avidin high affinity binding. The circular donor DNA that is not recombined with the acceptor DNA may also be extracted from the mixture. Since the circular donor DNA is incapable of replicating in a host insect cell and thus does not interfere with further functional analysis of the recombined baculoviral vector. The biotinylated oligonucleotide probe is preferably homologous to a GC-rich region of the circular donor DNA.

6. Propagation and Selection of the Recombinant Baculovirus

The recombinant baculovirus DNA selected in the above-described process is transfected into Sf9 insect cells using standard baculovirus construction techniques (Methods in Molecular Biology Vol. 39: Baculovirus Expression Protocols, Christopher D. Ricardson ed., Humana Press, Totowa, N.J. 1995).

The recombinant GUS baculovirus is passaged in the presence of G418 as described by Lerch and Friessen (1993) Nucleic Acid Res. 21:1753–1760. This is a positive selection step for propagation of the recombinant GUS baculovirus containing the Neo gene as a selectable marker.

7. Assessment of Recombinant Protein Production

The GUS activity is assayed by using the following protocol. The recombinant GUS baculovirus produced as described above is used to infect Sf9 insect cells. After 2 days the Sf9 cells are lysed in a solution of: 20 mM Tris pH8, 150 mM NaCl, 0.5% NP40 (10 ml of solution per gram of cells). The resulting lysate is serially diluted into PBS plus 150 ug/ml x-Gluc. Blue color in diluted samples indicates GUS activity. The terminal dilution of the recombinant GUS baculovirus produced by using the method of the present invention is compared with that of a recombinant GUS baculovirus produced by using conventional recombination techniques.

GUS protein expressed by the recombinant GUS baculovirus of the present invention is visualized by SDS gel electrophoresis and its levels of GUS expression are compared with those of GUS expression of a recombinant GUS baculovirus produced by using conventional recombination techniques. Briefly, Sf9 insect cells are infected with the recombinant GUS baculovirus of the present invention. After 2 days, the infected cells are lysed in a solution of: 20 mM Tris pH8, 150 mM NaCl, 0.5% NP40 (10 ml of solution per gram of cells). The lysate is loaded and run on an SDS-PAGE gel and stained with Coomassie blue. The intensity the 75 Kd GUS band from the recombinant GUS baculovirus produced by using the method of the present invention is compared with that from a recombinant GUS baculovirus produced by using conventional recombination techniques.

It will be apparent to those skilled in the art that various modifications and variations can be made in the compounds, compositions, kits, and methods of the present invention without departing from the spirit or scope of the invention. Thus, it is intended that the present invention covers the modifications and variations of this invention provided may come within the scope of the appended claims and their equivalents.

What is claimed is:

1. A method for generating a recombinant expression vector for expressing a donor DNA sequence, comprising:
   contacting a circular double-stranded donor DNA and a circular acceptor vector in the presence of a recombinase under conditions suitable for the circular double-stranded donor DNA and the circular acceptor vector to recombine to form a single fused circular vector that combines sequences of both the circular double-stranded donor DNA and the circular acceptor vector, thereby forming the recombinant expression vector for expressing the donor DNA sequence, wherein
   the circular double-stranded donor DNA comprises a donor DNA sequence, a single donor recombination site, and at least one selectable marker, but not including an origin of replication;
   the circular acceptor vector comprises an origin of replication and a single acceptor recombination site capable of recombining with the circular donor DNA; and
   the recombinase recognizes the donor and acceptor recombination sites and catalyzes fusion of the whole sequence of the circular double-stranded donor DNA into the circular acceptor vector.

2. The method according to claim 1, wherein the circular donor DNA further includes a promoter for regulating expression of the donor DNA.

3. The method of claim 2, wherein the promoter is derived from bacteria, yeast, insect, animal, plant or virus.

4. The method of claim 3, wherein the promoter is selected from the group consisting of E. coli lac and trp operons, the tac promoter, the bacteriophage $\lambda p^L$ promoter, bacteriophage T7 and SP6 promoters, β-actin promoter, insulin promoter, human cytomegalovirus (CMV) promoter, HIV-LTR, RSV-LTR, SV40 promoter, baculoviral polyhedrin and p10 promoter.

5. The method of claim 3, wherein the promoter is an inducible promoter.

6. The method of claim 5, wherein the inducible promoter is selected from the group consisting of tetracycline, heat shock, steroid hormone, heavy metal, phorbol ester, adenovirus E1A element, interferon, and serum inducible promoters.

7. The method according to claim 1, wherein the recombination sites on the circular donor DNA and the circular acceptor vector are both lox sites.

8. The method according to claim 1 further comprising steps of transforming, transfecting or transducing a host cell with the recombinant expression vector; and
   selecting the correctly fused recombinant vector based on the selectable phenotype conferred by the selectable marker gene carried by the circular double stranded donor DNA and recombined into the recombinant expression vector.

9. The method according to claim 8 further comprising:
   selecting the correctly fused recombinant vector by using a biotin-labeled oligonucleotide which is capable of hybridizing with circular double-stranded donor DNA.

10. The method according to claim 1, wherein the recombinase is selected from the group consisting of the bacteriophage P1 Cre recombinase, yeast FLP recombinase, Inti integrase, bacteriophage λ, phi 80, P22, P2, 186, and P4 recombinase, Tn3 resolvase, the Hin recombinase, the Cin recombinase, *E. coli* xerC and xerD recombinases, *Bacillus thuringiensis* recombinase, TpnI and the β-lactamase transposons, and the immunoglobulin recombinases.

11. The method of claim 1, the donor or the acceptor recombination site is a DNA sequence recognized by a site-specific recombinase to facilitate site-specific fusion between the circular donor DNA and an acceptor vector containing an acceptor recombination site.

12. The method of claim 1, wherein the donor or the acceptor recombination site is a recombination site recognized by a recombinase, a transposase or an integrase.

13. The method of claim 1, wherein the donor or the acceptor recombination site is a lox site that is recognized by the Cre recombinase of bacteriophage P1.

14. The method of claim 1, wherein the donor or the acceptor recombination site is selected from the group consisting of loxB, loxL, loxR, loxP, loxP3, loxP23, loxΔ86, loxΔ117, loxP511, and loxC2.

15. The method of claim 1, wherein the selectable marker is selected from the group consisting of β-galactosidase, fluorescent protein, secreted form of human placental alkaline phosphatase, β-glucuronidase, antibiotic resistance genes, yeast seletable markers leu2-d and URA3, apoptosis resistant genes, and antisense oligonucleotides.

16. The method of claim 1, wherein the circular donor DNA further includes an affinity tag.

17. The method of claim 16, wherein the affinity tag is selected from the group consisting of a polyhistidine tract, polyarginine, glutathione-S-transferase, maltose binding protein, a portion of staphylococcal protein A, protein A, and epitope tag.

18. The method of claim 16, wherein the affinity tag is an EE tag.

19. The method of claim 1, wherein the circular donor DNA further includes a polyadenylation signal.

20. The method of claim 1, wherein the circular acceptor vector further comprises a prokaryotic termination sequence selected from the group consisting of the T7 termination sequence, the bacteriophage λ $T_{INT}$, $T_{L1}$, $T_{L2}$, $T_{L3}$, $TR_1$, $TR_2$, and $T_{6S}$ termination signals.

21. The method of claim 1, wherein the circular acceptor vector is a mammalian expression vector.

22. The method of claim 21, wherein the mammalian expression vector contains one or more eukaryotic marker genes, a eukaryotic transcriptional and translational termination signal and a polyadenylation signal.

23. The method of claim 22, wherein the origin of replication functions in bacterial cells.

24. The method of claim 1, wherein the circular acceptor vector is a baculoviral vector.

25. The method of claim 24, wherein the baculoviral vector is a modified *Autographa californica* multiple nuclear polyhedrosis virus.

26. The method of claim 25, wherein the modified *Autographa californica* multiple nuclear polyhedrosis virus does not include a polyhedrin promoter.

27. The method of claim 1, wherein the circular donor DNA is generated by ligating a double-stranded linear donor DNA which includes the donor DNA sequence with a double-stranded linear driver DNA which includes the donor recombination site and the at least one selectable marker.

28. The method of claim 27, wherein the linear donor DNA and linear driver DNA contain matching restriction sites.

* * * * *